(12) United States Patent
Imamura

(10) Patent No.: US 10,514,028 B2
(45) Date of Patent: Dec. 24, 2019

(54) LIQUID DELIVERY DEVICE

(71) Applicant: Shimadzu Corporation, Kyoto (JP)

(72) Inventor: Shinya Imamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 183 days.

(21) Appl. No.: 15/756,746

(22) PCT Filed: Dec. 1, 2015

(86) PCT No.: PCT/JP2015/083705
§ 371 (c)(1),
(2) Date: Mar. 1, 2018

(87) PCT Pub. No.: WO2017/094097
PCT Pub. Date: Jun. 8, 2017

(65) Prior Publication Data
US 2018/0245581 A1    Aug. 30, 2018

(51) Int. Cl.
*F04B 49/06* (2006.01)
*F04B 11/00* (2006.01)
(Continued)

(52) U.S. Cl.
CPC ........ *F04B 49/065* (2013.01); *F04B 11/0058* (2013.01); *F04B 11/0075* (2013.01);
(Continued)

(58) Field of Classification Search
CPC ................ F04B 49/065; F04B 11/0058; F04B 11/0075; F04B 53/10; F04B 51/00;
(Continued)

(56) References Cited

U.S. PATENT DOCUMENTS 4,352,636 A   10/1982  Patterson et al.
4,681,513 A   7/1987   Saito et al.
(Continued)

FOREIGN PATENT DOCUMENTS

| JP | 1992061198 B2 | 9/1992 |
| JP | 1996023553 B2 | 3/1996 |
| JP | 2012031817 A  | 2/2012 |

OTHER PUBLICATIONS

International Search Report with English translation and Written Opinion dated Oct. 6, 2015 of corresponding International application No. PCT/JP2015/069389; 8 pgs.
(Continued)

*Primary Examiner* — Nathan C Zollinger
(74) *Attorney, Agent, or Firm* — Maier & Maier, PLLC

(57) ABSTRACT

A liquid feeding apparatus has a primary side pump and a secondary side pump, and an outlet part of the primary side pump and an inlet part of the secondary side pump are connected to each other via a check valve. A temporary side pump pressure sensor for detecting the pressure inside the pump chamber of the primary side pump and a secondary side pressure sensor for detecting the pressure inside the pump chamber of the secondary side pump are provided. The signal of the primary side pressure sensor and the signal of the secondary side pressure sensor are acquired after the suction operation of the primary side pump is terminated and before the discharge operation of the secondary side pump is terminated.

4 Claims, 5 Drawing Sheets

(51) Int. Cl.
*F04B 49/20* (2006.01)
*F04B 13/00* (2006.01)
*F04B 1/02* (2006.01)
*G01N 30/32* (2006.01)
*G01N 30/36* (2006.01)
*F04B 23/06* (2006.01)
*F04B 17/03* (2006.01)

(52) U.S. Cl.
CPC ............... *F04B 49/20* (2013.01); *F04B 1/02* (2013.01); *F04B 13/00* (2013.01); *F04B 17/03* (2013.01); *F04B 23/06* (2013.01); *G01N 30/36* (2013.01); *G01N 2030/326* (2013.01)

(58) Field of Classification Search
CPC .......... F04B 23/06; F04B 17/03; F04B 49/20; F04B 1/02; G01N 30/36; G01N 2030/326
See application file for complete search history.

(56) References Cited

U.S. PATENT DOCUMENTS

| | | | |
|---|---|---|---|
| 5,637,208 A | 6/1997 | Dourdeville | |
| 6,106,238 A * | 8/2000 | Ciavarini | F04B 49/065 417/216 |
| 6,712,587 B2 * | 3/2004 | Gerhardt | F04B 9/113 417/387 |
| 6,923,916 B1 * | 8/2005 | Hiraku | F04B 11/0083 210/101 |
| 7,063,785 B2 * | 6/2006 | Hiraku | F04B 11/0058 210/101 |
| 7,163,379 B2 * | 1/2007 | Mori | F04B 11/0075 417/6 |
| 7,189,320 B2 * | 3/2007 | Takao | F04B 9/02 210/101 |
| 7,588,423 B2 * | 9/2009 | Takao | F04B 11/0075 417/244 |
| 7,921,696 B2 * | 4/2011 | Takao | F04B 11/0058 210/101 |
| 8,123,496 B2 * | 2/2012 | Ishii | G01N 30/32 210/198.2 |
| 8,160,751 B2 * | 4/2012 | Pensak, Jr. | G01N 35/1097 210/198.1 |
| 8,191,405 B2 * | 6/2012 | Yasuhara | F04B 11/0075 73/61.56 |
| 9,410,543 B2 * | 8/2016 | Tokuo | F04B 13/00 |
| 2018/0274531 A1 * | 9/2018 | Yanagibayashi | F04B 23/06 |

OTHER PUBLICATIONS

Search Report dated Dec. 13, 2018 in corresponding European Application No. 15909727.8; 6 pages.

* cited by examiner

LIQUID DELIVERY DEVICE

FIELD

The present invention relates to a liquid feeding apparatus that performs liquid feeding, using two plunger pumps.

BACKGROUND

As a liquid feeding apparatus for feeding a mobile phase in a liquid chromatograph, there is an apparatus in which two plunger pumps are connected in series. A check valve is provided between a plunger pump on a front stage side (a primary side pump) and a plunger pump on a rear stage side (a secondary side pump). While the primary side pump is performing a liquid discharge operation, the check valve opens, and the liquid from the primary side pump is fed via the secondary side pump. While the primary side pump is performing a liquid discharge operation, the secondary side pump performs a suction operation of the liquid, and a part of the liquid discharged from the primary side pump is sucked by the secondary side pump. Thus, the liquid having a flow rate corresponding to the value obtained by subtracting the suction flow rate of the secondary side pump from the discharge flow rate of the primary side pump is fed from an outlet part of the secondary side pump.

After the discharge operation of the primary side pump is terminated, the suction and discharge operations of the primary side pump and the secondary side pump are switched, and while the secondary side pump is performing the discharge operation, the primary side pump performs the suction operation. At this time, the check valve between the primary side pump and the secondary side pump is closed, and the flow rate of the liquid fed through the outlet part of the secondary side pump becomes the discharge flow rate of the secondary side pump. By this operation, the liquid is continuously fed from the outlet part of the secondary side pump.

When the suction and discharge operations of the primary side pump and the secondary side pump are switched immediately after the suction operation of the liquid using the primary side pump is terminated, the pressure inside a pump chamber of the primary side pump, which has been performing the suction operation just before, becomes lower than the pressure inside a pump chamber of the secondary side pump. Thus, the check valve does not open until the pressure inside the pump chamber of the primary side pump becomes equal to or higher than the pressure inside the pump chamber of the secondary side pump, and a flow fluctuation (pulsating flow) occurs.

Therefore, it has been proposed and practiced that a pressure sensor for detecting the pressure inside the pump chamber of the primary side pump and the pressure inside the pump chamber of the secondary side pump is provided, and after the suction operation of the liquid in the primary side pump is terminated, during the period until the discharge operation in the secondary side pump is terminated, until the pressure inside the pump chamber of the primary side pump becomes equal to the pressure inside the pump chamber of the secondary side pump, a preloading operation of driving the primary side pump to the discharge side is performed (see Patent Document 1).

Patent Document 1: U.S. Pat. No. 5,637,208

SUMMARY

In the preloading operation, generally, it is conceivable to acquire detection signals of two pressure sensors for detecting pressures inside the pump chambers of the primary side pump and the secondary side pump at regular time intervals, take a difference between them, and perform a feedback-control of a stepping motor of the primary side pump until the difference value falls within a predetermined range.

However, noise is contained in the detection signal of the pressure sensor, and when the noise is large, there is a problem in which the preloading operation is terminated in a state in which the pressure inside the pump chamber of the primary side pump does not reach the pressure inside the pump chamber of the secondary side pump, or a problem in which the pressure inside the pump chamber of the primary side pump exceeds the pressure inside the pump chamber of the secondary side pump during the preloading operation, and pulsating flow occurs.

Therefore, an object of the invention is to reduce the noise of a detection signal acquired from the pressure sensor and to prevent the pulsating flow.

A liquid feeding apparatus according to the invention includes: a pump unit which has a primary side pump and a secondary side pump configured to perform suction and discharge of liquid by driving a distal end of a plunger in one direction in a pump chamber, an outlet part of the primary side pump and an inlet part of the secondary side pump being connected to each other via a check valve; a temporary side pump pressure sensor which detects the pressure inside the pump chamber of the primary side pump; a secondary side pressure sensor which detects the pressure inside the pump chamber of the secondary side pump; a drive control unit which controls operation of the primary side pump and the secondary side pump to perform a suction operation of the secondary side pump during the discharge operation of the primary side pump and to perform a suction operation of the primary side pump during the discharge operation of the secondary side pump; a preloading operation unit which acquires a signal of the primary side pressure sensor and a signal of the secondary side pressure sensor after the suction operation of the primary side pump is terminated and before the discharge operation of the secondary side pump is terminated, and executes a preloading operation of driving the primary side pump to the discharge side, until the pressure inside the pump chamber of the primary side pump becomes substantially equal to the pressure inside the pump chamber of the secondary side pump, on the basis of an acquired signal; and a preloading time determining unit which determines a time allocated to the preloading operation, on the basis of a preset liquid feeding flow rate. The preloading operation unit is configured to acquire the signal from the primary side pressure sensor and the secondary side pressure sensor at an acquisition frequency determined depending on the preloading time determined by the preloading time determining unit.

The time (preloading time) allocated to the preloading operation is determined depending on the set liquid feeding flow rate. When the liquid feeding flow rate is low, since the driving speed of the secondary side pump is slow and the discharge time of the secondary side pump becomes longer, it is possible to lengthen the preloading time after completion of the suction operation. Conversely, when the liquid feeding flow rate is large, since the driving speed of the secondary side pump is high and the discharge time of the secondary side pump also becomes shorter, it is not possible to lengthen the preloading time after completion of the suction operation.

When the preloading time is short, since it is necessary to make the pressure inside the pump chamber of the primary side pump reach the pressure inside the pump chamber of the secondary side pump in a short time, it is necessary to quickly operate the plunger. Therefore, at the time of the preloading operation, since the detection signal of the primary side pressure sensor rapidly rises, in order to perform the feedback control with high accuracy, it is necessary to acquire the signal of the pressure sensor at high speed.

On the other hand, when the preloading time can be lengthened, since the pressure inside the pump chamber of the primary side pump only may be made to reach the pressure inside the pump chamber of the secondary side pump chamber within that time, the plunger of the primary side pump can be operated slowly. Therefore, at the time of the preloading operation, since the detection signal of the primary side pressure sensor gently increases, even when the signal of the pressure sensor is acquired at a very high speed, accuracy of the feedback control is not greatly affected.

However, in order to precisely perform the feedback control of the preloading operation under any liquid feeding condition, it is common that the detection signal of the pressure sensor is acquired at a frequency corresponding to the shortest preloading time.

Here, the detection signal of the pressure sensor slightly fluctuates. When the acquisition frequency (resolution) of the signal is low, since the slightly fluctuating signal is averaged and acquired, noise of the acquired signal is small. However, when the acquisition frequency of signal is high, the acquired signal is likely to be affected by slight fluctuation, and the noise increases. When the noise of the signal acquired from the pressure sensor is large, it is determined that the pressure inside the pump chamber of the primary side pump has reached despite not reaching the pressure inside the pump chamber of the secondary side pump. In contrast, it is determined that the pressure inside the pump chamber of the primary side pump has not reached despite reaching the pressure inside the pump chamber of the secondary side pump. Thus, the preloading operation cannot be performed normally, which causes a pulsation. Therefore, at the time of the preloading operation, it is important not to raise the acquisition frequency of the signals from the pressure sensor beyond necessity.

In view of the above, the liquid feeding apparatus according to the invention includes a preloading time determining unit which determines the time allocated to the preloading operation, on the basis of a preset liquid feeding flow rate, and the preloading operation unit is configured to acquire the signal from the primary side pressure sensor and the secondary side pressure sensor at an acquisition frequency determined depending on the preloading time determined by the preloading time determining unit. Accordingly, the acquisition of the signal is performed from the pressure sensors of the primary side and the secondary side at the acquisition frequency corresponding to the preloading time, and signals are not acquired at a frequency higher than necessity. As a result, it is possible to reduce the noise caused by the acquisition frequency of signal.

DETAILED DESCRIPTION OF THE DRAWINGS

A preferred embodiment of a liquid feeding apparatus according to the invention further includes: an acquisition frequency data holding unit which holds a relation between an acquisition frequency of acquiring signals from a primary side pressure sensor and a secondary side pressure sensor during a preloading operation and a length of a preloading time allocated to the preloading operation as acquisition frequency data; and an acquisition frequency determining unit which determines the acquisition frequency on the basis of the acquisition frequency data held in the acquisition frequency data holding unit, when the preloading time is determined by the preloading time determining unit. The preloading operation unit is configured to acquire signals from the primary side pressure sensor and the secondary side pressure sensor at the acquisition frequency determined by the acquisition frequency determining unit.

A further preferred embodiment of the liquid feeding apparatus according to the invention further includes a preload determining unit which takes a difference between signals acquired from the primary side pressure sensor and the secondary side pressure sensor during the preloading operation and determines whether a difference value is within a preset predetermined range. The preloading operation unit is configured to complete the preloading operation when the difference value of the signals acquired from both sensors falls within a predetermined range.

Hereinafter, an embodiment of a liquid feeding apparatus according to the invention will be described with reference to the drawings.

Figure 1:
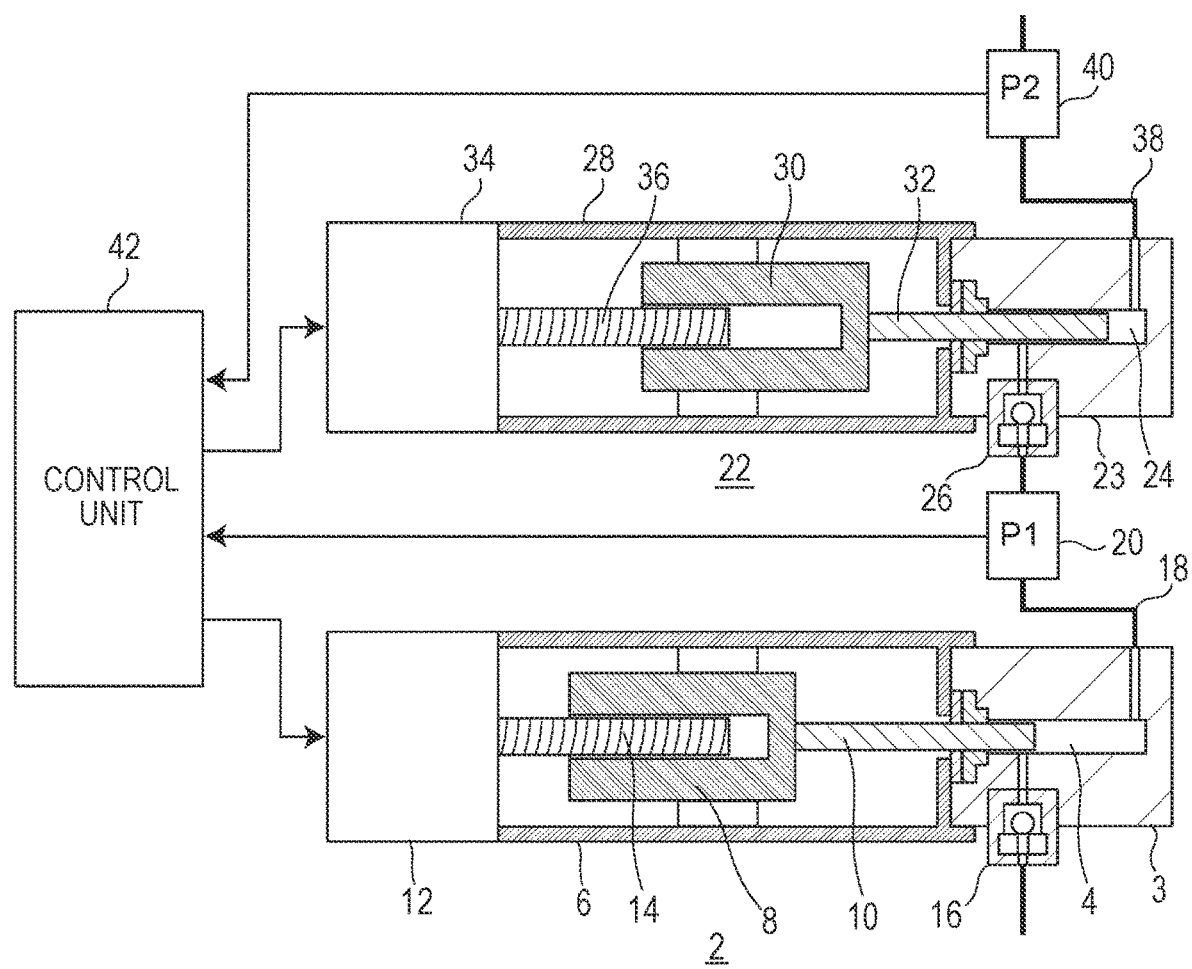
FIG. 1 is a cross-sectional configuration diagram schematically illustrating a configuration of an embodiment of a liquid feeding apparatus.

First, the configuration of the liquid feeding apparatus will be described with reference to FIG. 1.

The liquid feeding apparatus of this embodiment includes a primary side pump 2 and a secondary side pump 22. The primary side pump 2 and the secondary side pump 22 are connected in series to each other.

The primary side pump 2 includes a pump head 3 having a pump chamber 4 therein, and a pump body 6. The pump head 3 is provided at a distal end of the pump body 6. The pump head 3 is provided with an inlet part which allows the liquid to flow into the pump chamber 4, and an outlet part which allows the liquid to flow out of the pump chamber 4. A check valve 16 for preventing backflow of the liquid is provided in the inlet part of the pump head 3.

The distal end of a plunger 10 is slidably inserted into the pump chamber 4. A proximal end of the plunger 10 is held by a crosshead 8 housed in the pump body 6. The crosshead 8 moves inside the pump body 6 by the rotation of a feed screw 14 in one direction (a left-right direction in the drawing), and the plunger 10 moves in one direction accordingly. A primary side pump driving motor 12 which rotates the feed screw 14 is provided at the proximal end portion of the pump body 6. The primary side pump driving motor 12 is a stepping motor.

The secondary side pump 22 includes a pump head 23 having a pump chamber 24 therein, and a pump body 28. The pump head 23 is provided at the distal end of the pump body 28. The pump head 23 is provided with an inlet part which allows the liquid to flow into the pump chamber 24, and an outlet part which allows the liquid to flow out of the pump chamber 24. A check valve 26 for preventing backflow of the liquid is provided in the inlet part of the pump head 23.

The distal end of a plunger 32 is slidably inserted into the pump chamber 24. The proximal end of the plunger 32 is held by a crosshead 30 housed in the pump body 28. The crosshead 30 moves inside the pump body 28 by the rotation of a feed screw 36 in one direction (the left-right direction in the drawing), and the plunger 32 moves in one direction accordingly. A secondary side pump driving motor 34 which rotates the feed screw 36 is provided at the proximal end portion of the pump body 28. The secondary side pump driving motor 34 is a stepping motor.

The inlet part of the pump head 3 is connected to a container (not illustrated) that stores the liquid to be fed via a flow path. An inlet part of the pump head 23 is connected to an outlet part of the pump head 3 via a connecting flow path 18. A primary side pressure sensor 20 for detecting the pressure (P1) in the pump chamber 4 is provided on the connecting flow path 18.

An outlet flow path 38 is connected to the outlet part of the pump head 23. The outlet flow path 38 leads to, for example, an analysis flow path of a liquid chromatograph. A secondary side pressure sensor 40 for detecting the pressure (P2) in the pump chamber 24 is provided on the outlet flow path 38.

The operation of the primary side pump driving motor and the secondary side pump driving motor 34 is controlled by a control unit 42. The detected signals obtained by the primary side pressure sensor 20 and the secondary side pressure sensor 40 are acquired into the control unit 42. The control unit 42 controls the operation of the primary side pump driving motor 12 on the basis of the signals from the primary side pressure sensor 20 and the secondary side pressure sensor 40 at the time of a preloading operation to be described later.

To briefly explain the operation of the liquid feeding apparatus, when the discharge operation of the liquid using the primary side pump 2 is started, the check valve 16 is closed, the check valve 26 is opened, and the liquid from the outlet part of the pump head 3 is discharged to the outlet flow path 38 through the connecting flow path 18, the check valve 26, and the pump chamber 24. At this time, the secondary side pump 22 performs the suction operation at a flow rate smaller than the discharge flow rate of the primary side pump 2, and a part of the liquid discharged from the pump head 3 is stored in the pump chamber 24.

When the discharge operation of the liquid using the primary side pump 2 is terminated, the discharge operation of the liquid using the secondary side pump 22 is started. When the discharge operation of the liquid using the secondary side pump 22 is started, since the pressure inside the pump chamber 24 becomes higher than the pressure inside the pump chamber 4, the check valve 26 is closed. While the discharge operation of the liquid is being performed by the secondary side pump 22, the suction operation and the preloading operation of the liquid are performed in the primary side pump 2. When the discharge operation of the liquid using the secondary side pump 22 is terminated, the discharge operation of the liquid using the primary side pump 2 is started.

The preloading operation of the primary side pump 2 is performed in order to prevent occurrence of defective liquid feeding when the liquid discharge operation of the primary side pump 2 is started after the liquid discharge operation of the secondary side pump 22 is terminated. That is, immediately after the suction operation of the primary side pump 2 is terminated, the pressure inside the pump chamber 4 becomes lower than the pressure inside the pump chamber 24. Therefore, even when the suction and discharge operations of the primary side pump 2 and the secondary side pump 22 are switched immediately after the suction operation of the primary side pump 2 is terminated, until the pressure inside the pump chamber 4 becomes equal to or higher than the pressure inside the pump chamber 24, the liquid is not fed from the primary side pump 2, and the liquid feeding flow rate of the liquid feeding apparatus drops sharply, resulting in a defective liquid feeding.

Therefore, before the discharge operation of the secondary side pump 22 is terminated, the primary side pump 2 executes a preloading operation for keeping the pressure inside the pump chamber 4 at the same pressure as the pressure inside the pump chamber 24. In the preloading operation, the control unit 42 acquires a signal from the primary side pressure sensor 20 and a signal from the secondary side pressure sensor 40, and performs discharge and driving, while performing the feedback control of the primary side pump 2 so that the pressure inside the pump chamber 4 becomes equal to the pressure inside the pump chamber 24.

Figure 2:
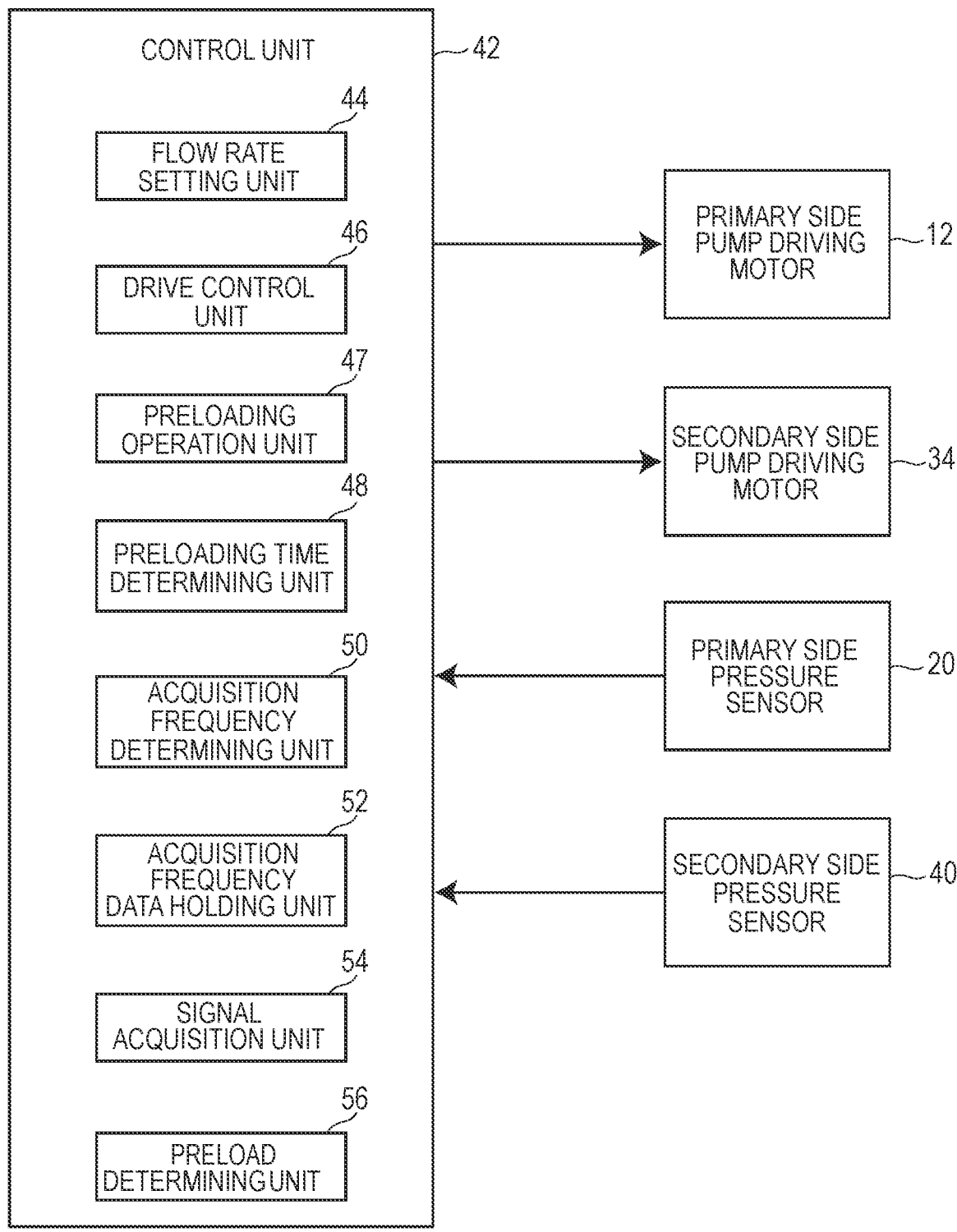
FIG. 2 is a block diagram schematically illustrating the configuration of the embodiment.

The configuration of the control unit 42 will be described in more detail with reference to FIG. 2.

The control unit 42 is achieved by a dedicated computer provided in the apparatus or a general-purpose personal computer. The control unit 42 includes a flow rate setting unit 44, a drive control unit 46, a preloading operation unit 47, a preloading time determining unit 48, an acquisition frequency determining unit 50, an acquisition frequency data holding unit 52, a signal acquisition unit 54, and a preload determining unit 56. The flow rate setting unit 44, the drive control unit 46, the preloading operation unit 47, the preloading time determining unit 48, the acquisition frequency determining unit 50, the signal acquisition unit 54, and the preload determining unit 56 are functions obtained by executing a program stored in the storage device provided in the control unit 42. The acquisition frequency data holding unit 52 is a function achieved by a partial region of the storage device provided in the control unit 42.

The flow rate setting unit 44 sets the liquid feeding flow rate of the liquid feeding apparatus on the basis of the information which is input by the user.

The drive control unit 46 controls the operations of the primary side pump driving motor 12 and the secondary side pump driving motor 34 so that the flow rate of the liquid fed through the outlet flow path 38 becomes a set value of the liquid feeding flow rate which is set by the flow rate setting unit 44.

The preloading operation unit 47 causes the primary side pump 2 to execute the preloading operation during the discharge operation of the secondary side pump 22. The preloading operation is executed within the preloading time determined by a preloading time determining unit 48 to be described later. The preloading operation refers to an operation of increasing the pressure inside the pump chamber 4, by moving the plunger 10 of the primary side pump 2 after the suction operation in the discharge direction.

When the liquid feeding flow rate is set by the flow rate setting unit 44, the preloading time determining unit 48 determines the time which is assigned to the preloading operation, on the basis of the set value. The driving speed of the secondary side pump 22 is determined by the set value of the liquid feeding flow rate. Therefore, when the liquid feeding flow rate increases, the driving speed of the secondary side pump 22 becomes faster accordingly, and the time required for the discharge operation of the secondary side pump 22 becomes shorter.

During the discharge operation of the secondary side pump 22, the primary side pump 2 executes the suction operation and the preloading operation. In this embodiment, since the primary side pump 2 performs the suction operation at the maximum driving speed, the time required for the suction operation of the primary side pump 2 is constant. Therefore, the time (preloading time) allocated to the preloading operation of the primary side pump 2 is the time obtained by subtracting the time (constant) required for the suction operation of the primary side pump 2 from the time required for the discharge operation of the secondary side pump 22.

On the basis of the preloading time determined by the preloading time determining unit 48 and the acquisition frequency data acquired in advance, the acquisition frequency determining unit 50 determines the acquisition frequency (acquisition speed) of the signal from the primary side pressure sensor 20 and the secondary side pressure sensor 40 during the preloading time. The acquisition frequency data is held in the acquisition frequency data holding unit 52.

The acquisition frequency data is set such that the acquisition frequency is low as the preloading time is long and the acquisition frequency is high as the preloading time is short. Acquisition frequency data was created on the basis of data obtained by experiments. Specifically, the acquisition frequency data is created so that an acquisition frequency is an acquisition frequency in which a noise value is always equal to or less than a predetermined allowable value, and in which the signal is acquired at a time interval shorter than the time required for the motor of the primary side pump to rotate by a minimum rotation angle. The allowable value of noise is, for example, the maximum value in a predetermined range compared with the difference value between the primary side pressure sensor 20 and the secondary side pressure sensor 40 in a preloading determination to be described later. The time required for the minimum rotation angle of the motor of the primary side pump is obtained from a maximum preloading required volume and the preloading time estimated by the compression rate or the compression volume of the compressed solvent, and the liquid feed pressure.

At the time of the preloading operation of the primary side pump 2, the signal acquisition unit 54 acquires signals of the primary side pressure sensor 20 and the secondary side pressure sensor 40 with the acquisition frequency determined by the acquisition frequency determining unit 50.

The preload determining unit 56 takes the difference between the signals of the primary side pressure sensor 20 and the secondary side pressure sensor 40 acquired by the signal acquisition unit 54, and determines whether the difference value is within a predetermined range. The predetermined range is, for example, 0 to 0.05 MPa. When the preload determining unit 56 determines that the difference value between the signals of the primary side pressure sensor 20 and the secondary side pressure sensor is within the predetermined range, the preloading operation unit 47 terminates the preloading operation.

Figure 3:
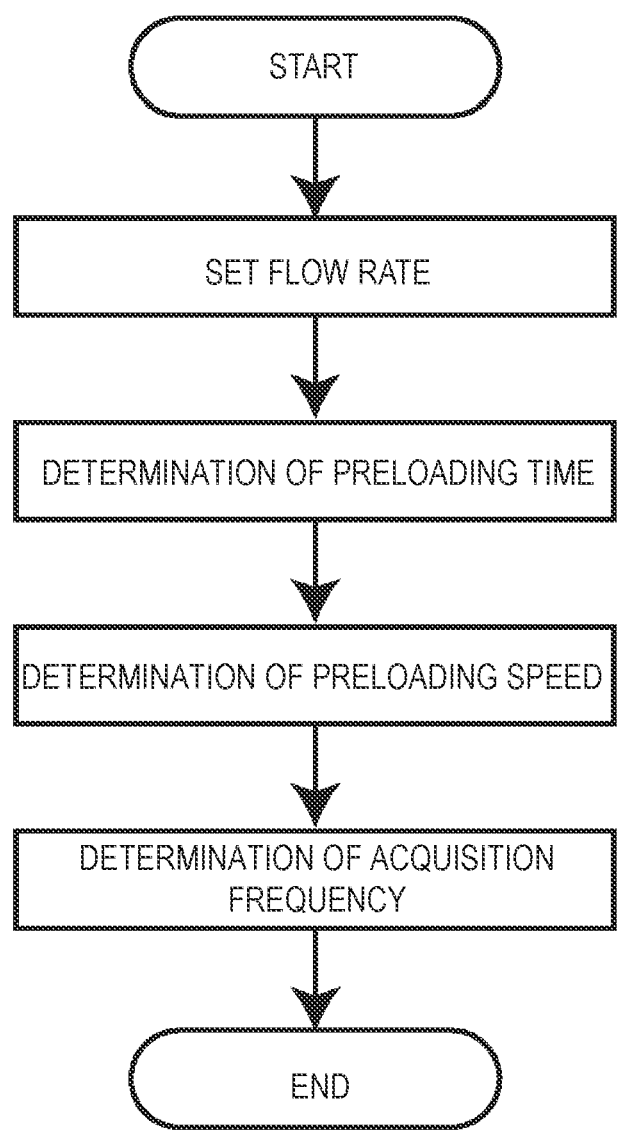
FIG. 3 is a flowchart illustrating an initial setting operation according to the embodiment.

Next, the initial setting operation of the liquid feeding apparatus will be described with reference to the flowchart of FIG. 3.

In the initial setting, first, a flow rate to be fed through the outlet flow path 38 is set on the basis of input information from the user. When the liquid feeding flow rate is set, the preloading time assigned to the preloading operation of the primary side pump 2 is determined on the basis of the flow rate. When the preloading time is determined, the driving speed (preloading speed) of the primary side pump motor 12 for completing the preloading operation within the preloading time is determined. When the preloading speed is determined, the acquisition frequency of the signals from the primary side pressure sensor 20 and the secondary side pressure sensor 40 is determined on the basis of the preloading speed.

Figure 4:
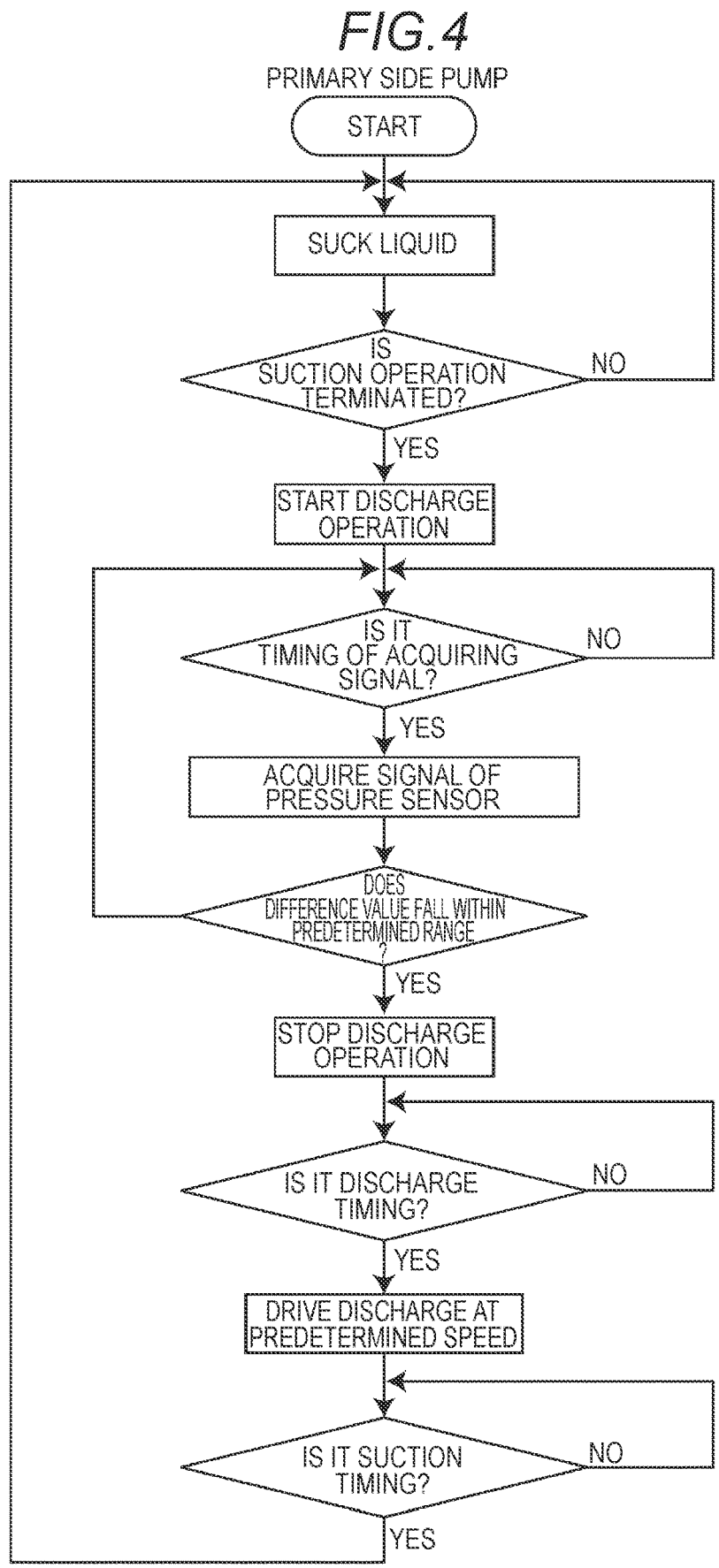
FIG. 4 is a flowchart illustrating an operation control of a primary side pump according to the embodiment.
Figure 5:
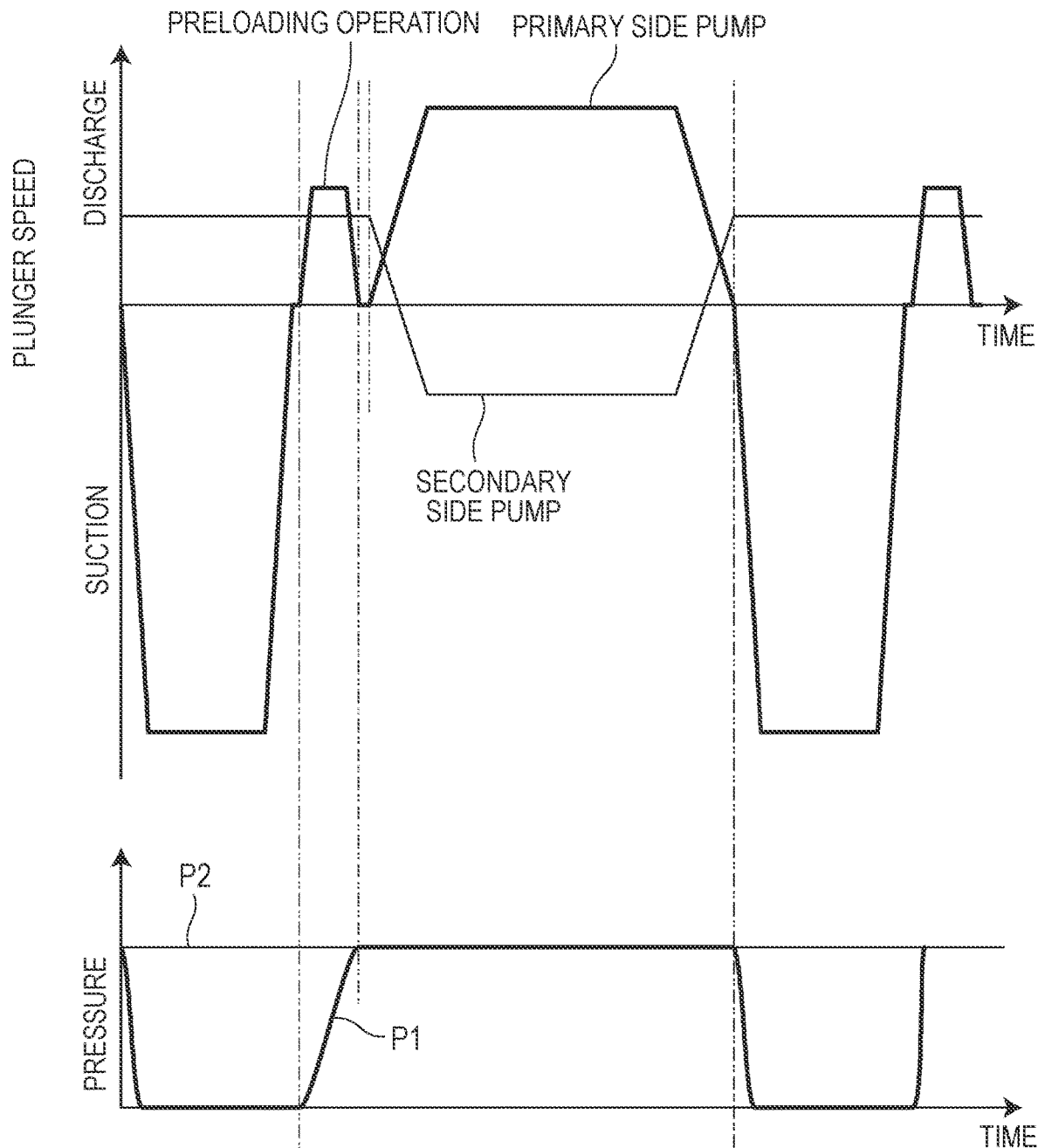
FIG. 5 is a graph illustrating operations of a primary side pump and a secondary side pump of the embodiment, and a detected value (P1) of the primary side pressure sensor and a detected value (P2) of the secondary side pressure sensor according to the operation.

Next, the operation of the primary side pump during liquid feeding will be described with reference to FIGS. 4 and 5. In FIG. 5, an upper graph illustrates a time change in the plunger speed of the primary side pump (thick line) and the secondary side pump (thin line), and a lower graph illustrates a time change of the detected pressure P1 of the primary side pressure sensor 20 and the detected pressure P2 of the secondary side pressure sensor 40.

The secondary side pump 22 repeatedly executes the suction operation and the discharge operation at a constant speed corresponding to the set liquid feeding flow rate. When the secondary side pump 22 starts the discharge operation, the primary side pump 2 starts the suction operation of the liquid. This suction operation is performed by driving the plunger 10 to the suction side at the maximum possible design speed.

After the suction operation of the primary side pump is terminated, the preloading operation is started. First, the discharge operation of the primary side pump 2 is started. Specifically, the plunger 10 is driven to the discharge side (the right side in FIG. 1) at a speed (preloading speed) which is set on the basis of the time (preloading time) assigned to the preloading operation. After the discharge operation is started, the signals from the primary side pressure sensor 20 and the secondary side pressure sensor 40 are acquired with a preset acquisition frequency, and the difference between the signal intensities is taken each time. The discharge operation is continued until the difference value falls within a preset predetermined range, and when the difference value falls within the predetermined range, the discharge operation is terminated. As a result, the pressure (P1) inside the pump chamber 4 of the primary side pump 2 and the pressure (P2) inside the pump chamber 24 of the secondary side pump 22 become substantially the same.

After completion of the preloading operation, when there is a discharge timing of the primary side pump 2, that is, timing of switching between the suction and discharge operations of the primary side pump 2 and the secondary side pump 22 is obtained, the plunger 10 is driven to the discharge side at a predetermined speed depending on the set flow rate to perform the liquid feeding. In the secondary side pump 22, the suction operation is performed at a flow rate smaller than that of the primary side pump 2, and a part of the liquid discharged from the primary side pump 2 is stored in the pump chamber 24. Further, the flow rate corresponding to the value obtained by subtracting the suction flow rate of the secondary side pump 22 from the discharge flow rate from the primary side pump 2 becomes the flow rate of the liquid feeding performed through the outlet flow path 38.

The invention claimed is:
1. A liquid feeding apparatus comprising:
   a pump unit which has a primary side pump and a secondary side pump configured to perform suction and discharge of liquid by driving a distal end of a plunger in one direction in a pump chamber, an outlet part of the primary side pump and an inlet part of the secondary side pump being connected to each other via a check valve;

a primary side pressure sensor which detects the pressure inside the pump chamber of the primary side pump;

a secondary side pressure sensor which detects the pressure inside the pump chamber of the secondary side pump;

a drive control unit which controls operation of the primary side pump and the secondary side pump to perform a suction operation of the secondary side pump during the discharge operation of the primary side pump and to perform a suction operation of the primary side pump during the discharge operation of the secondary side pump;

a preloading operation unit which acquires a signal of the primary side pressure sensor and a signal of the secondary side pressure sensor after the suction operation of the primary side pump is terminated and before the discharge operation of the secondary side pump is terminated, and executes a preloading operation of driving the primary side pump to the discharge side, until the pressure inside the pump chamber of the primary side pump becomes substantially equal to the pressure inside the pump chamber of the secondary side pump, on the basis of the acquired signals; and a preloading time determining unit which determines a time allocated to the preloading operation, on the basis of a preset liquid feeding flow rate, wherein the preloading operation unit is configured to acquire the signals from the primary side pressure sensor and the secondary side pressure sensor at an acquisition frequency determined depending on the preloading time determined by the preloading time determining unit.

2. The liquid feeding apparatus according to claim 1, further comprising:

an acquisition frequency data holding unit which holds a relation between an acquisition frequency of acquiring signals from the primary side pressure sensor and the secondary side pressure sensor during the preloading operation and a length of a preloading time allocated to the preloading operation, as acquisition frequency data; and an acquisition frequency determining unit which determines the acquisition frequency on the basis of the acquisition frequency data held in the acquisition frequency data holding unit, when the preloading time is determined by the preloading time determining unit, wherein the preloading operation unit is configured to acquire signals from the primary side pressure sensor and the secondary side pressure sensor at the acquisition frequency determined by the acquisition frequency determining unit.

3. The liquid feeding apparatus according to claim 1, further comprising:

a preload determining unit which takes a difference between signals acquired from the primary side pressure sensor and the secondary side pressure sensor during the preloading operation and determines whether a difference value is within a preset predetermined range, wherein the preloading operation unit completes the preloading operation when the difference value of the signals acquired from both sensors falls within a predetermined range.

4. The liquid feeding apparatus according to claim 2, further comprising:

a preload determining unit which takes a difference between signals acquired from the primary side pressure sensor and the secondary side pressure sensor during the preloading operation and determines whether a difference value is within a preset predetermined range, wherein the preloading operation unit completes the preloading operation when the difference value of the signals acquired from both sensors falls within a predetermined range.

* * * * *